United States Patent
Lehoux et al.

(10) Patent No.: US 6,814,929 B2
(45) Date of Patent: Nov. 9, 2004

(54) ANTIBACTERIAL COMPOSITION FOR DIFFUSING TO COMBAT BACTERIA CONTAINED IN THE AIR, A METHOD OF DIFFUSING SUCH A COMPOSITION

(75) Inventors: Jannick Lehoux, Thuit Signol (FR); Corinne Gomez, Louviers (FR)

(73) Assignee: Produits Berger (FR)

( * ) Notice: Subject to any disclaimer, the term of this patent is extended or adjusted under 35 U.S.C. 154(b) by 468 days.

(21) Appl. No.: 09/789,152

(22) Filed: Feb. 20, 2001

(65) Prior Publication Data

US 2002/0110479 A1 Aug. 15, 2002

(30) Foreign Application Priority Data

Dec. 14, 2000 (FR) .............................. 00 16338

(51) Int. Cl.[7] .............................................. A61L 9/00
(52) U.S. Cl. .............................. 422/4; 422/5; 422/123; 424/76.3; 424/76.4; 516/4
(58) Field of Search ...................... 422/45, 123; 516/4; 424/76.3, 76.4

(56) References Cited

U.S. PATENT DOCUMENTS 4,983,635 A   1/1991   Martin 6,136,771 A * 10/2000 Taylor et al. ............... 510/388
6,451,748 B1 * 9/2002 Taylor et al. ............... 510/131
6,569,907 B1 * 5/2003 Kubo et al. .................. 516/4

FOREIGN PATENT DOCUMENTS

| FR | 2179664 | 11/1973 |
| FR | 2540382 | 8/1984 |
| FR | 2598615 | 11/1987 |
| FR | 2779509 | 12/1999 |
| GB | 2181351 | 4/1987 |
| JP | 9-030906 | 2/1997 |

* cited by examiner

Primary Examiner—Krisanne Jastrzab
(74) Attorney, Agent, or Firm—Bachman & LaPointe, P.C.

(57) ABSTRACT

The invention provides a composition for diffusion in the air of an enclosure to be treated to combat the bacteria contained in the air of the enclosure. The composition contains 2-phenylphenol and natural and/or synthetic thymol dissolved in a solvent such as isopropyl alcohol, for example. The invention also provides a method of combating the bacteria in the air of an enclosure to be treated, which method includes a step of diffusing the antibacterial composition into the air of the enclosure. Finally, the invention provides the use of a catalytic combustion flask for implementing such a method.

17 Claims, 3 Drawing Sheets

FIG. 5

ANTIBACTERIAL COMPOSITION FOR DIFFUSING TO COMBAT BACTERIA CONTAINED IN THE AIR, A METHOD OF DIFFUSING SUCH A COMPOSITION

FIELD OF THE INVENTION

The present invention relates to a composition for diffusing to combat bacteria contained in the air in an enclosure to be treated. The invention also relates to a method of combating bacteria comprising a step of diffusing said composition. Finally, the invention relates to the use of a catalytic combustion flask for implementing such a method.

In the present invention, combating bacteria covers both bactericidal activity (which term is used to designate a substance having the property of killing bacteria), and also bacteriostatic activity (which term is used to designate a substance that shows the development of such bacteria). Those two forms of activity are covered by the term "antibacterial".

BACKGROUND OF THE INVENTION

Presently known techniques for combating bacteria implement disinfectants which are generally applied directly to contaminated surfaces.

Of the wide range of compounds known for conserving an antibacterial preservative, mention can be made of 2-phenylphenol, known commercially as "preventol O extra" or indeed "E 231". This compound is used in the preparation of numerous disinfectants and detergents and can also be used for preserving a large number of products. 2-phenylphenol possesses a vast spectrum of effectiveness against bacteria, yeasts, molds, etc.

Extra red thyme essence, in its commercial form, is another compound known for having antibacterial activity. It is used in certain pharmaceuticals such as toothpastes, antiseptics for mouthwashes, . . . . Extra red thyme essence contains 40% up to a maximum of 52% by weight of natural thymol, about 20% of para-cymene, about 3% to 4% of carvacrol, with the remainder being constituted by terpenes and alcohols.

Synthetic thymol is also known.

These two compounds are thus well known as antibacterials and they act by contact on surfaces to be treated.

Devices also exist for purifying air. They are in the form of ionizers, purifiers, sprays, or aerosol cans.

Ionizers are more specifically adapted to combating dust. The drawback is that using them contributes to emitting ozone and that can be dangerous for man.

Air purifiers act more specifically on dust in the air.

Sprays and aerosols cans serve to diffuse the substances they contain in air in the form of more or less fine droplets, which substances act likewise mainly by contact, given the dimensions of the droplets.

These large-sized droplets provide a specific surface area for action that is smaller than that which could be obtained with a greater quantity of droplets that are smaller.

Nevertheless, there is nothing to prevent antibacterial compositions being diffused by means of sprays or aerosol cans. However, any antibacterial effects of such devices against bacteria contained in the air within an enclosure has yet to be observed or demonstrated. Furthermore, that mode of diffusion remains very local and can only be curative. Also, concentrations of active substances remain quite high and thus relatively harmful and/or unpleasant for the user.

OBJECTS AND SUMMARY OF THE INVENTION

The present invention seeks to mitigate the above-mentioned drawbacks and proposes a composition for diffusing in the air of an enclosure to be treated in order to combat bacteria contained in the air of said enclosure.

According to the invention, this composition comprises 2-phenylphenol and natural and/or synthetic thymol dissolved in a solvent comprising isopropyl alcohol, for example.

Surprising synergy has been found to exist between these two compounds, making it possible to obtain antibacterial action on germs in the air that is considerably greater than the antibacterial action achieved by diffusing either 2-phenylphenol or thymol on its own.

Generally, the composition comprises a proportion by weight lying in the range about 0.05% to 1% of 2-phenylphenol and a proportion by weight lying in the range about 0.05% to 5% of thymol.

Concentrations of 2-phenylphenol and of thymol below the minimum values given above would probably not suffice to achieve the desired ambitious target which is fixed in arbitrary manner as reducing the bacteria contained in the air of an enclosure to be treated by least about 75%, and preferably by at least 80% within 24 hours of an antibacterial composition of the invention being diffused for a relatively short length of time, about 20 minutes.

Concentrations of 2-phenylphenol and of thymol greater than the maximum values given above would naturally enable the looked-for antibacterial effect to be obtained, and it is therefore entirely possible to envisage diffusing antibacterial compositions of the invention having concentrations by weight of these two compounds that are greater or even much greater.

Nevertheless, these maximum values have been determined to take account of various parameters, in particular cost parameters, so as to ensure that the cost in active components is not excessive commercially speaking, and also for other reasons of a more practical nature.

When antibacterial compositions of the invention are to be diffused by catalytic combustion, it is essential to avoid premature aging of the catalytic burner used.

Whenever possible, antibacterial compositions of the invention must be diffused in such a manner as to avoid generating smoke or compounds that are known to be toxic for the user; as a subsidiary point, the odor generated must be pleasing to the user.

Other criteria can also be taken into consideration when limiting the concentration by weight of one and/or the other of the antibacterial compounds used in the context of the present invention, such as the solubility or the appearance of the composition.

In an advantageous version, the composition comprises a proportion by weight lying in the range about 0.1% to 0.3% of 2-phenylphenol and a proportion by weight lying in the range about 0.2% to 2% of thymol.

In a preferred version, the composition comprises a proportion by weight equal to about 0.2% of 2-phenylphenol and a proportion by weight lying in the range about 0.5% to 1% of thymol.

In both cases, the quantities of 2-phenylphenol and of thymol are well below those of the antibacterial substances commonly employed with known diffusion methods.

The method of the invention gives rise to far fewer secondary effects for the user, and presents toxicity that is much less than that of known methods.

In a preferred embodiment of the invention, the composition comprises a total proportion by weight of 2-phenylphenol plus thymol lying in the range about 0.1% to 5%, and preferably in the range about 0.2% to 1.2%.

The total quantity of active substances employed in the context of the present invention is well below the prior art, and can achieve genuine effectiveness at concentrations by weight that are of the order of one-tenth those of the prior art.

The present invention also provides a method of combating bacteria contained in the air of an enclosure to be treated. This method comprises a step of diffusing an antibacterial composition in the air of the enclosure.

According to the invention, the composition comprising 2-phenylphenol and thymol dissolved in a solvent is diffused in such a manner that said solvent is to be found entirely in the gaseous state.

Advantageously, said composition is diffused by means of a catalytic combustion burner, the solvent being combustible and comprising, for example, isopropyl alcohol.

In the implementation of the method of the invention of combating bacteria, the invention also provides the use of a catalytic combustion flask adapted to contain a combustible composition and to receive a catalytic combustion burner on a collar fixed to its neck, said burner having a substantially axial cavity that is downwardly open and that receives a mesh dipping in said composition, the burner optionally presenting a substantially axial annular groove extending from the top surface of the burner and separating an annular peripheral zone supporting the catalyst from a catalyst-free central zone forming a vaporization zone, and/or a channel for putting the top portion of the cavity receiving the wick into communication with the atmosphere.

BRIEF DESCRIPTION OF THE DRAWINGS

Other advantages and features of the invention appear from the following description of non-limiting examples given with reference to the accompanying figures, in which.

MORE DETAILED DESCRIPTION

Figure 1:
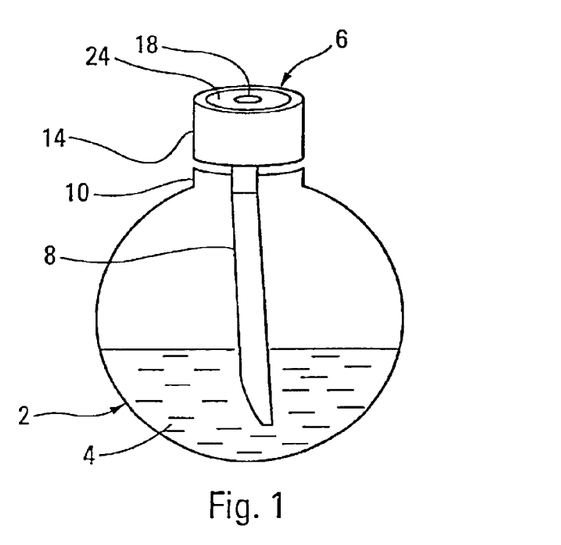
FIG. 1 is a diagrammatic elevation view of a flask fitted with a catalytic combustion burner which can be used for implementing the method of the present invention.

FIG. 1 shows a catalytic combustion flask 2 used for implementing the tests described below.

The catalytic combustion flask 2 is adapted to contain a combustible composition 4 and to receive at its top end a catalytic combustion burner 6 that receives a wick 8 dipping in said composition 4.

The flask 2 can be a flask of arbitrary shape having a neck 10 to which the burner 6 is fitted.

The combustible composition 4 comprises a solvent which generally belongs to the alcohol family and which is constituted by isopropyl alcohol, for example, however it could also comprise any other suitable liquid fuel. This liquid fuel is preferably such that its vaporization and catalytic combustion do not give rise to substances that are very toxic for the user under normal conditions of diffusion.

Diffusion is performed by vaporizing the solvent while hot.

The combustible composition 4 of the invention may optionally further comprise one or more other compounds that are natural or synthetic, e.g. compounds that are commonly diffused by means of a catalytic combustion system, and in particular fragrances.

The wick 8 is any conventional wick, e.g. a cotton wick. The wick can also be a wick of inorganic material, e.g. a wick of inorganic fibers.

Figure 2:
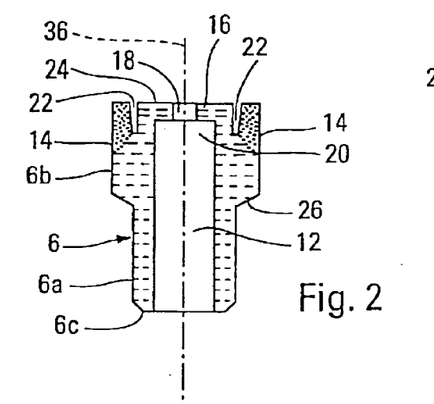
FIG. 2 is a diagrammatic view in axial section and on a larger scale showing the burner of FIG. 1 in a preferred implementation of the method of the present invention.

As shown in detail in FIG. 2, the catalytic combustion burner 6 is a burner made of porous ceramic material, e.g. based on kaolin.

In its bottom portion 6a, the burner 6 has a substantially axial cavity 12 adapted to receive a wick 8 for bringing the combustible composition 4 to the burner 6. The cavity 12 opens out to the bottom end 6c of the burner 6 and extends axially over a large part of the axial extent of the burner 6.

In its top portion 6b, the burner 6 has an annular peripheral zone 14 supporting a catalyst, e.g. based on a metal taken from group VIII of the periodic table for classifying the elements. The annular zone 14 surrounds a central zone 16 which is free of catalyst and which forms a vaporization zone.

In the example shown in FIG. 2, the burner 6 has at least one open channel 18 in its top portion 6b, putting the top portion 20 of the cavity 12 into communication with the atmosphere.

In this example and in conventional manner, the burner 6 has a substantially axial annular groove 22 extending downwards from the top surface 24 of the burner 6 on a diameter that is greater than the diameter of the cavity 12.

This annular groove 22 provides a clear separation between the annular peripheral zone 14 which supports the catalyst and the central zone 16 of the top portion 6b.

Figure 3:
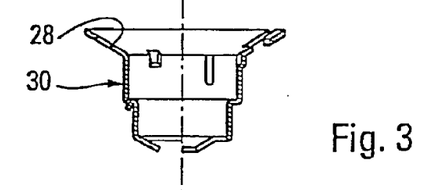
FIG. 3 is a view similar to FIG. 2 showing an embodiment of a support for the FIG. 2 burner.

The burner 6 has a peripheral shoulder 26 received by a complementary shoulder 28 of a support 30 shown in FIG. 3.

The support 30 can be inserted directly into the neck 10 of the flask 2.

Figure 4:
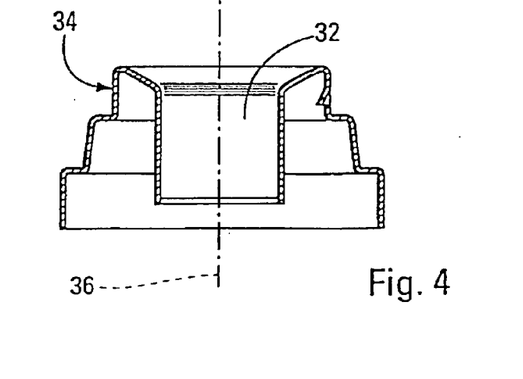
FIG. 4 is a view similar to FIG. 2 showing an embodiment of a collar suitable for receiving the support of FIG. 3.
Figure 5:
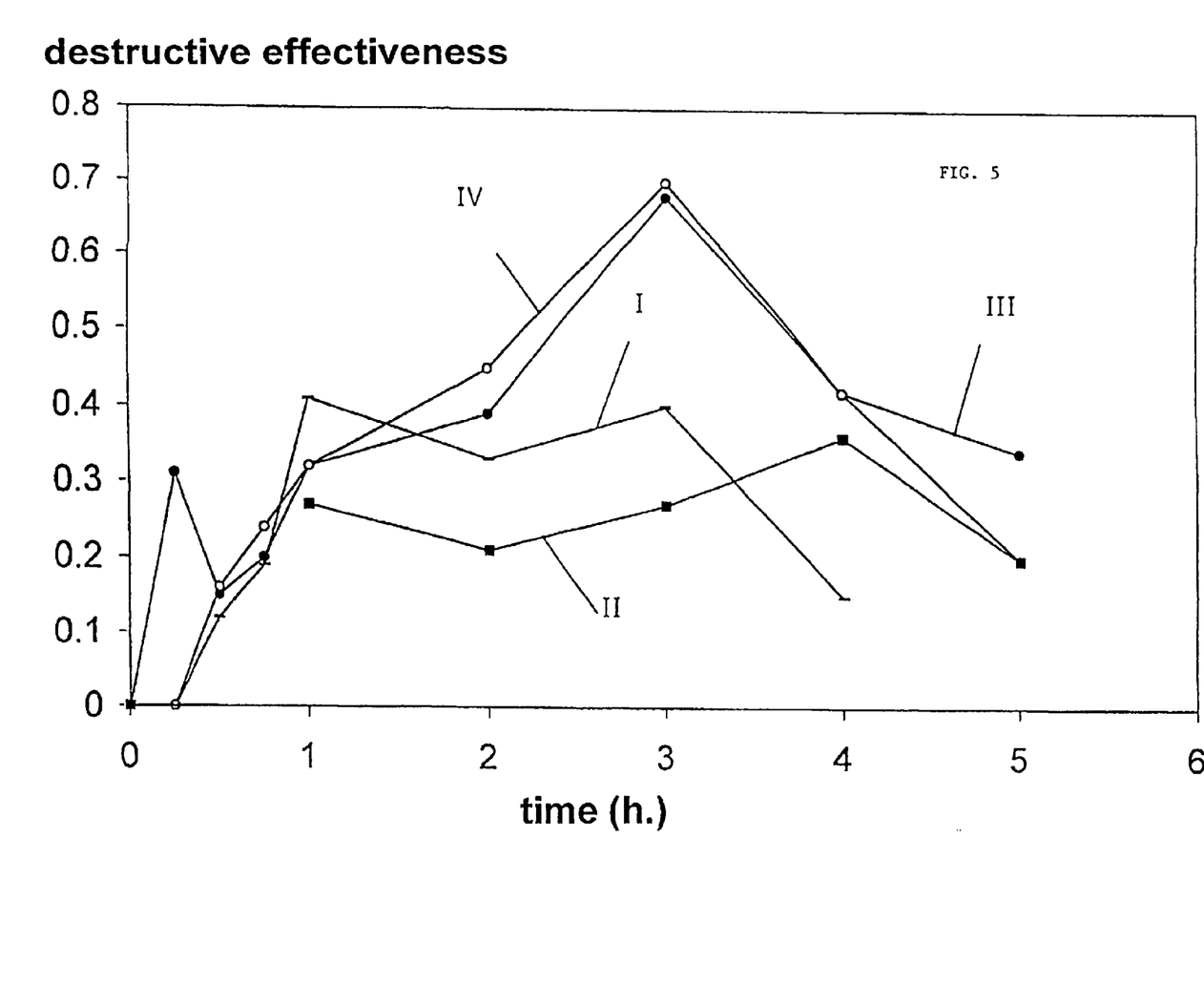
FIG. 5 is a graph with curves I to IV showing measurements of destructive effectiveness as a function of time plotted in hours during tests 1 to 4.

As a general rule, the support 30 is inserted into the central hole 32 of a collar 34 of the kind shown diagrammatically in FIG. 4, said collar 34 being adapted to be fixed to the neck 10 of the flask 2.

The main effect of the support 30 is to encourage the user of the burner 6 to put the support 30 and the burner 6 properly in place on the collar 34 on the axis 36 that is common to the neck 10, the collar 34, the support 30, and the burner 6.

There is nothing to prevent other flask structures being associated with a catalytic burner. In particular, the various flasks described in international patent application PCT/FR99/00937 can advantageously be used in the context of the present invention.

Various tests have been performed and have demonstrated the intense antibacterial activity against the bacteria contained in the air of an enclosure to be treated of a composition comprising 2-phenylphenol and thymol dissolved in a solvent, and have revealed the genuine synergy that is obtained in the combat against bacteria contained in the air of an enclosure when such a composition is diffused in such a manner that the solvent is to be found entirely in the gaseous state in said air.

In general, the antibacterial activity of a composition is determined by measuring its destructive effectiveness (ED) as defined by the formula $ED=\log_{10}(N_0/N)$ where $N_0$ is the initial bacteria count as measured prior to diffusing the composition in question, and N is the bacteria count as measured at time t starting from the beginning of said diffusion.

Although the destructive effectiveness obtained during the first few hours following diffusion of each tested composition can in some cases reach values of the order of 0.7, that is not particularly advantageous in the event of effectiveness subsequently falling off very quickly due to recontamination. Such a result corresponds to the result that can be obtained using conventional contact treatments of the kind described above.

In the absence of any standardized measuring apparatus for providing reliable measurements, tests 1 to 8 were performed in application of the following mode of operation: the composition to be tested was put into a diffuser that was placed on a table, the table being placed in the middle of a room having a volume of 50 cubic meters ($m^3$).

To measure bacterial population, air was sampled by means of an aerobiocollector placed at 2.30 meters (m) from the flask, and slightly lower than said flask.

An aerobiocollector is a device that sucks in air at a rate of 100 liters per minute (1/min) and that contains a trap such as a Petri dish containing agarose, enabling the bacteria contained in the air to be recovered.

In each of the tests, the initial bacterial population was measured prior to implementing catalytic combustion.

During tests 1 to 7, the composition under test was introduced into a flask of the type shown in FIG. 1, said flask being provided with a catalytic combustion burner of the kind described in FIG. 2.

Catalytic combustion was performed continuously for 25 minutes and then interrupted. Bacterial population was then measured at regular time intervals starting from the beginning of catalytic combustion, and then the corresponding ED value was determined.

The solvent used in all of the compositions for tests 1 to 7 was isopropyl alcohol at a concentration of 90% by volume in water.

It has been known for a long time that an antibacterial substance can be diffused by catalytic combustion. However, tests 2 to 4 serve to quantify the corresponding antibacterial activity more precisely.

Initially, a first test or test 1 was performed to determine the antibacterial activity of the solvent on its own.

Test 1 was performed by introducing isopropyl alcohol only in the flask, under the operating mode described above.

The measurements taken during this first test are represented by curve I in FIG. 5.

Curve I shows low destructive effectiveness ED, well below the looked-for values of at least 0.6.

The maximum value for ED was reached after 1 hour, and it was about 0.41. This means that at most 60% of the commonplace germs in the air such as *Rhodotorula rubra* (yeasts), *Aspergillus niger*, Pencillium (molds) are destroyed 1 hour after lighting the catalytic combustion burner.

Low antibacterial activity continued for about 3 to 4 hours after the burner was lighted, after which it can be seen that the air became progressively recontaminated. ED dropped to zero after about 5 hours, which means that the air in the vicinity of the diffuser had been progressively recontaminated and had returned to its initial bacterial population ($N_0$).

The results of test 1 indicate that isopropyl alcohol does indeed have some effect on microbial contamination in the air, which effect is probably restricted to the vicinity of the diffuser and is of very short duration.

The minimum looked-for objective to be achieved was the destruction of at least three-quarters of the bacteria initially present after a period of at least 24 hours had elapsed since the antibacterial composition began to be diffused, and this corresponds to a looked-for minimum value of ED of about 0.60, which value was never reached in test 1.

The ED measured in test 2 for a composition containing 1% by weight of essence of red thyme, i.e. having at most 0.52% by weight of natural thymol, was relatively low.

As indicated by curve II in FIG. 6 which shows how the measured values of destructive effectiveness varied as a function of time during test 2, the maximum ED reached, 23 hours after catalytic combustion had been started, was 0.52. 55 hours after combustion started, ED had dropped to zero.

Comparing the ED values obtained in the context of tests 1 and 2 shows that the presence of red thyme essence in isopropyl alcohol improves the antibacterial activity of the composition very slightly: in the second test a maximum of 70% of the bacteria contained in the air were destroyed as compared with only 60% in test 1.

However, the minimum values looked for in the context of the present invention were not achieved.

It should nevertheless be observed that introducing red thyme essence in isopropyl alcohol prolonged the antibacterial activity of the composition over time; ED dropped down to zero after 55 hours had elapsed and not after only 5 hours from the beginning of catalytic combustion, as was the case in test 1.

This confirms the antibacterial activity of red thyme essence, which activity is known in any event.

During tests 3 and 4, two compositions containing respectively 0.2% and 1% by weight of 2-phenylphenol were tested.

The curves of ED as a function of time that were obtained, respectively referenced III (test 3) and IV (test 4) in FIG. 5 are entirely comparable.

Multiplying the concentration of 2-phenylphenol in the composition by 5 did not lead to any quantifiable improvement in ED, either in terms of immediate antibacterial activity (curative effect) or in terms of remanent antibacterial activity (preventative effect).

Furthermore, although ED reached a maximum ED value of about 0.7, thus enabling the number of bacteria to be reduced by 80%, it can be seen that this effect occurred very quickly, 3 hours after catalytic combustion was started.

No remanent effect of the antibacterial activity was discovered: in tests 3 and 4, the ED value fell back to zero 8 hours after catalytic combustion had been started.

Consequently, the antibacterial activity of compositions containing 2-phenylphenol is completely unsatisfactory compared with the requirements needed to purify the air in an enclosure.

It can thus be seen that in tests 1 to 4, the compositions tested did not in general enable a large reduction to be achieved in the bacterial population. Although destructive effectiveness did indeed reach a value of 0.7 during tests 3 and 4, the antibacterial activity of those compositions did not last for long.

It is very likely that antibacterial activity remained localized around the catalytic combustion flask such that the air in the enclosure became recontaminated as soon as said combustion ceased. Furthermore, recontamination takes place all the faster when only few bacteria have been destroyed.

The insufficient antibacterial activity of the compositions in tests 1 to 4 in terms of antibacterial use is corroborated by additional measurements performed on the pathogenic bacteria used in standard tests (e.g. those specified by AFNOR, the French Standards Institution), where the measured values of ED were zero.

Tests 1 to 4 thus illustrate what can be considered as being the state of the art at the date of the present invention.

The object looked for by the present invention has been arbitrarily fixed at reducing the number of bacteria initially present in the air of the enclosure to be treated by at least 75%, with the expected value for destructive effectiveness ED 24 hours after starting catalytic combustion being at least 0.6 and preferably greater than 0.7.

This object was indeed achieved under the conditions of tests 5 to 8.

Test 5, was applied to a composition of the invention comprising both 2-phenylphenol and red thyme essence in respective concentrations by weight of 0.2% and of 1% (or a maximum 0.5% natural thymol).

Figure 6:
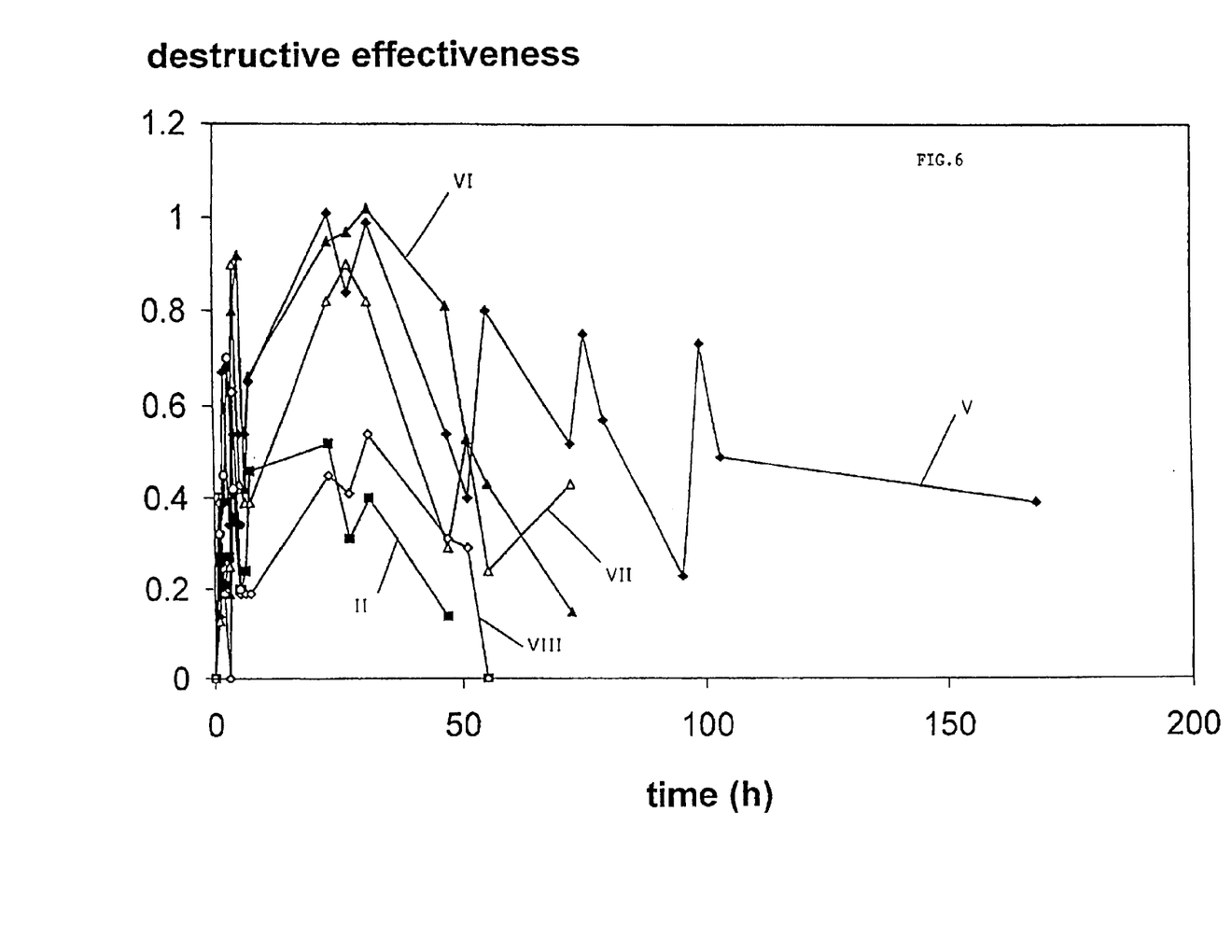
FIG. 6 is a graph showing curves II and V to VIII of measurements of destructive effectiveness as a function of time plotted in hours during tests 2 and 5 to 8.

Curve V in FIG. 6 shows that ED as measured during test 5 reached a maximum value of 1.01, which means that more than 90% of the bacteria were destroyed, and that this occurred 23 hours after the start of catalytic combustion.

Test 5 clearly demonstrates surprising and unexpected synergy between red thyme essence and 2-phenylphenol, where such synergy could not be expected from the results of previous tests 2, 3, and 4.

23 hours after the start of catalytic combustion, ED reached at best a value of 0.52 in test 2, whereas in tests 3 and 4 it had already dropped to zero.

Test 5 also reveals a surprising and particularly advantageous remanence phenomenon. Furthermore, the ED value of the composition of test 5, as measured at 55 hours, was 0.8, which still corresponds to the bacterial population being reduced by 84%, which is well above the duration target which was set arbitrarily at 24 hours.

168 hours after the start of catalytic combustion, the ED value of test 5 was still 0.4, i.e. a reduction of 60%.

It can be assumed that this remanence is the result of rapid and intense antibacterial action throughout the entire volume of the treated enclosure.

Test 6 was performed with a composition of the invention comprising 2-phenylphenol and synthetic thymol, at respective concentrations by weight of 0.2% and of 1%. The ED measurements taken over time are represented by curve VI in FIG. 6.

The maximum ED value achieved at 31 hours was 1.02 and again corresponds to the bacterial population being reduced by more than 90%.

The results presented by test 6 are entirely satisfactory with respect to the requirements fixed by the inventors. Nevertheless, the remanence phenomenon was less marked than it was during test 5.

During test 7, the quantity of synthetic thymol was halved compared with that used in test 6.

With reference to curve VII in FIG. 6, it can be seen that the ED values obtained in test 7 were comparable to those obtained in test 6, as was the case previously in tests 3 and 4 in which only the concentration of 2-phenylphenol was varied.

Reducing the quantity of artificial thymol appears to have little real influence on the level of antibacterial activity of the composition under test. Thus, a very small quantity of thymol combined with 2-phenylphenol makes it possible to obtain the looked-for antibacterial activity under conditions that are advantageous in terms of cost of materials.

However, comparing tests 5 and 7 in which the respective proportions of natural thymol and of artificial thymol were both 0.5% by weight, shows that the remanent effect is much more marked, and thus that antibacterial activity is much better over time, when the composition is made up using red thyme essence.

This reveals a new synergy provided by the composition of the invention, which synergy is probably due to one or more of the compounds other than natural thymol contained in red thyme essence.

It can thus be assumed that amongst said compounds, carvacrol which is an isomer of thymol and is also known as being an antibacterial agent, participates in this second synergy.

In test 8, diffusion was performed differently. The antibacterial composition under test comprised 0.2% by weight of 2-phenylphenol and 1% by weight of red thyme essence dissolved in water and it was introduced into a receptacle that was placed at the same position in the room as the device that was used during previous tests 1 to 7. Thereafter, the receptacle was heated so as to maintain the composition at a temperature lying in the range 40° C. to 80° for a period of 2 hours.

Bacterial population was measured before, during, and then after diffusion of the composition under test using the same sampling techniques as for tests 1 to 7.

As shown by curve VIII in FIG. 6, the maximum ED value obtained in test 8 was 0.63 and it was reached at is 4 hours.

Nevertheless it can be assumed that better results could have been obtained in test 8 by heating a composition containing a little more antibacterial agent to a higher temperature.

After 4 hours, the antibacterial activity of the composition containing 0.2% by weight of 2-phenylphenol and 1% by weight of red thyme essence was considerably higher when diffused by catalytic combustion than it was in test 8, particularly given that diffusion in test 5 was continued for about one-fifth of the time that it was continued in test 8, and the amount of solvent vaporized was slightly less, being 12 grams (g) in test 5 and 13.1 g in test 8.

This demonstrates the existence of a third synergy associating this antibacterial composition with the particularly fine diffusion that is obtained by vaporization using a catalytic combustion flask.

The data obtained during tests 1 to 8 is summarized in the table below, in which the abbreviations "ess.", "2-PP", "synth.", and "*" mean respectively: "red thyme essence", "2-phenylphenol", "synthetic thymol", and "not measured".

| Test | Antibacterial composition (% by weight) | ED at 23 h | ED max | ED zero | ED at 168 h |
|------|------------------------------------------|------------|--------|---------|-------------|
| 1 | solvent only | 0 | 0.41 | at 5 h | 0 |
| 2 | 1% (ess.) | 0.52 | 0.52 | at 55 h | 0 |
| 3 | 0.2% (2-PP) | 0 | 0.68 | at 8 h | 0 |
| 4 | 1% (2-PP) | 0 | 0.70 | at 8 h | 0 |
| 5 | 0.2% (2-PP) +1% (ess.) | 1.01 | 1.01 | >168 h | 0.4 |
| 6 | 0.2% (2-PP) +1% (synth.) | 0.95 | 1.02 | >70 h | * |
| 7 | 0.2% (2-PP) +0.5% (synth.) | 0.82 | 0.9 | >70 h | * |
| 8 | 0.2% (2-PP) +1% (ess.) | 0 | 0.63 | at 55 h | 0 |

Comparing the ED values of tests 5 and 8 shows clearly that diffusing an antibacterial composition of the invention by means of a catalytic combustion system makes it possible to destroy more than 90% of the bacteria present in the air, a rate that is never reached using the method of diffusion of test 8.

Surprisingly, this excellent antibacterial activity presented by catalytic combustion diffusion associated with the antibacterial composition of the present invention presents an extremely advantageous remanent effect.

This remanent effect is particularly remarkable with antibacterial composition used in test 5 since 7 days after the start of catalytic combustion ED was still about 0.4, even though catalytic combustion had been continued only for the very short duration of 25 minutes.

It can thus be seen that using a catalytic combustion system to diffuse a composition associating in particular 2-phenylphenol and thymol at very low concentrations by weight guarantees diffusion of said compositions that is fine and effective, making it possible not only to reduce the bacterial population over the time that follows diffusion of these compositions, but also provides remanence over time.

This observation has been corroborated by additional analysis performed used pathogenic bacteria: *Staphylococcus aureus* and *Pseudomonas aeruginosa* are two of the five microorganisms used in the AFNOR standards for measuring and validating antibacterial activity of a compound that makes contact.

Three plates with a determined *Pseudomonas aeruginosa* count seeded thereon were placed respectively close to, 50 cm away, and 1 m away from a flask of the type shown in FIG. 1 containing the same composition as in test 5 and fitted with a catalytic combustion burner of the kind described in FIG. 2.

After the composition of test 5 had been diffused for 30 minutes, a large reduction (specifically 89%)in the *Pseudomonas aeruginosa* count was observed on the plate situated close to the flask; this reduction diminished thereafter: it was 45% for the plate situated at 50 cm and no more than 7% for the plate situated at 1 m.

Comparable results were obtained with the test performed on *Staphylococcus aureus,* using the same protocol as that described above for *Pseudomonas aeruginosa.*

The reduction in the *Staphylococcus aureus* count was 94% for the plate situated close to the flask, 46% for the plate at 50 cm, and 10% for the plate at 1 m.

These last two experiments show clearly that while using only very small quantities of 2-phenylphenol and of red thyme essence, significant antibacterial activity can be obtained on two pathogenic micro-organisms even in the absence of any direct contact with the above-mentioned composition, which microorganisms are also known for having high levels of resistance to chemical and physical attack; resistance which is clearly greater than that of commonplace germs in the air. It can be deduced that the same pathogenic germs, if present in the air of the enclosure, would also have been destroyed.

This demonstrates that the antibacterial activity of the composition and of the method of the present invention on germs contained in the air of an enclosure to be treated is intense not only against commonplace germs in the air, but also against resistant pathogenic germs that might be present in the air.

It is therefore possible to envisage using the invention to combat not only commonplace germs in the air such as *Rhodotorula rubra, Aspergillus niger,* Pencillium, but also pathogenic bacteria including *Staphylococcus aureus* and *Pseudomonas aeruginosa.*

The invention thus presents the twofold advantage of using only a small amount of active compound and thus of diffusing an antibacterial composition that presents no danger for the health of the user, with this being by means of a surprising third synergy effect between the antibacterial composition and the method whereby it is diffused.

This synergy effect appears to be even more marked when red thyme essence is used.

The savings achieved by using small quantities of active compounds are further improved by the method being implemented relatively quickly.

Naturally, the present invention is not limited to the embodiments described above and numerous changes and modifications can be applied thereto without going beyond the domain of the invention.

In particular, the length of time for which the composition of the invention is diffused can be increased, thereby making it possible to achieve the maximum destructive effectiveness value ED more quickly.

Furthermore, it seems likely that the antibacterial composition and the method of the present invention also have a significant effect against microbes, in particular in terms of combating fungi, including their spores, viruses, and bacterial spores.

What is claimed is:

1. A composition for diffusion in the air of an enclosure to be treated to combat the bacteria contained in the air of said enclosure, wherein said composition comprises 2-phenylphenol, natural and/or synthetic thymol and a solvent that is combustible and is diffused by vaporizing while hot, the 2-phenylphenol and thymol being dissolved in said solvent.

2. A composition according to claim 1, wherein said solvent is isopropyl alcohol.

3. A composition according to claim 1, wherein the proportion by weight of 2-phenylphenol lies generally in the range of about 0.05% to 1.0%, and the proportion by weight of thymol lies generally in the range of about 0.05% to 5.0%.

4. A composition according to claim 1, wherein the proportion by weight of 2-phenylphenol lies generally in the range of about 0.1% to 0.3% and the proportion by weight of thymol lies generally in the range of about 0.2% to 2.0%.

5. A composition according to claim 1, wherein the proportion by weight of 2-phenylphenol is about 0.2% and the proportion by weight of thymol lies generally in the range of about 0.5% to 1.0%.

6. A composition according to claim 1, comprising a total proportion by weight of 2-phenylphenol plus thymol lying in the range from about 0.1% to 5.0%.

7. A composition according to claim 1, comprising a total proportion by weight of 2-phenylphenol plus thymol in the range of about 0.2% to 1.2%.

8. A composition according to claim 1, containing red thyme essence.

9. A composition according to claim 1, further containing at least one natural or synthetic compound.

10. A composition according to claim 9, wherein said at least one natural or synthetic compound comprises a fragrance material.

11. A method of combating bacteria contained in the air of an enclosure to be treated, the method comprising diffusing an antibacterial composition into the air of said enclosure, wherein said composition comprises 2-phenyphenol and natural and/or synthetic thymol dissolved in a solvent that is combustible and is diffused by vaporizing while hot is heated so as to be diffused by vaporization of said solvent.

12. A method according to claim 11, wherein said composition is diffused by means of a catalytic combustion burner.

13. A method according to claim 12, wherein said solvent is isopropyl alcohol.

14. A method according to claim 11, wherein said diffusion combats commonplace germs in the air such as *Rhodotorula rubra, Aspergillus niger*, Pencillium and pathogenic bacteria including *Staphylococcus aureus* and *Pseudomonas aeruginosa*.

15. A method according to claim 12, further comprising receiving said catalytic combustion burner on a collar fixed to a neck of a catalytic combustion flask, said flask being adapted to contain said composition, and said burner having a substantially axial cavity that is downwardly open and that receives a mesh dipping in said composition.

16. A method according to claim 12, further comprising providing said burner with a substantially axial annular groove extending from a top surface of the burner and separating an annular peripheral zone supporting a catalyst from a catalyst-free central zone forming a vaporization zone.

17. A method according to claim 12, further comprising providing said burner with a channel for putting a top portion of a cavity receiving a wick into communication with the atmosphere.

* * * * *

UNITED STATES PATENT AND TRADEMARK OFFICE
CERTIFICATE OF CORRECTION

| | | |
|---|---|---|
| PATENT NO. | : 6,814,929 B2 | Page 1 of 1 |
| APPLICATION NO. | : 09/789152 | |
| DATED | : November 9, 2004 | |
| INVENTOR(S) | : Jannick Lehoux et al. | |

It is certified that error appears in the above-identified patent and that said Letters Patent is hereby corrected as shown below:

Column 10,
Line 47, after "combat" delete "the".

Signed and Sealed this

Twentieth Day of June, 2006

JON W. DUDAS
*Director of the United States Patent and Trademark Office*